US012640397B2

(12) United States Patent
Lee et al.

(10) Patent No.: US 12,640,397 B2
(45) Date of Patent: May 26, 2026

(54) IONIC LIQUID, ELECTROLYTE FOR SECONDARY BATTERY INCLUDING IONIC LIQUID, AND SECONDARY BATTERY INCLUDING ELECTROLYTE

(71) Applicants: SK ON CO., LTD., Seoul (KR); SK INNOVATION CO., LTD., Seoul (KR)

(72) Inventors: Jin Hong Lee, Daejeon (KR); Hong Won Lee, Daejeon (KR); In Haeng Cho, Daejeon (KR); Sung Jin Kim, Daejeon (KR)

(73) Assignees: SK ON CO., LTD., Seoul (KR); SK INNOVATION CO., LTD., Seoul (KR)

( * ) Notice: Subject to any disclaimer, the term of this patent is extended or adjusted under 35 U.S.C. 154(b) by 651 days.

(21) Appl. No.: 17/974,392

(22) Filed: Oct. 26, 2022

(65) Prior Publication Data

US 2023/0129153 A1 Apr. 27, 2023

(30) Foreign Application Priority Data

Oct. 26, 2021 (KR) ........................ 10-2021-0143193

(51) Int. Cl.

| | |
|---|---|
| ***H01M 10/0567*** | (2010.01) |
| ***C07C 311/48*** | (2006.01) |
| ***C07F 9/572*** | (2006.01) |
| ***C07F 9/6506*** | (2006.01) |
| ***H01M 4/62*** | (2006.01) |
| ***H01M 10/0525*** | (2010.01) |
| *H01M 4/02* | (2006.01) |

(52) U.S. Cl.

CPC ....... *H01M 10/0567* (2013.01); *C07C 311/48* (2013.01); *C07F 9/572* (2013.01); *C07F 9/6506* (2013.01); *H01M 4/62* (2013.01); *H01M 10/0525* (2013.01); *H01M 2004/027* (2013.01); *H01M 2300/0045* (2013.01)

(58) Field of Classification Search

None

See application file for complete search history.

(56) References Cited

U.S. PATENT DOCUMENTS

| | | | |
|---|---|---|---|
| 2010/0209782 A1 | 8/2010 | Choi et al. | |
| 2010/0304225 A1 | 12/2010 | Pascaly et al. | |
| 2017/0288269 A1 | 10/2017 | Moganty et al. | |

FOREIGN PATENT DOCUMENTS

| | | | |
|---|---|---|---|
| CN | 109119687 | A | 1/2019 |
| CN | 110600802 | A | 12/2019 |
| CN | 109119687 | B | 9/2020 |
| CN | 112993380 | A | 6/2021 |
| EP | 2860183 | A1 | 4/2015 |
| KR | 10-2010-0051794 | A | 5/2010 |
| KR | 10-2012-0080154 | A | 7/2012 |
| KR | 10-2018-0131580 | A | 12/2018 |
| KR | 10-2021-0111019 | A | 9/2021 |
| WO | 2019/081907 | A1 | 5/2019 |

OTHER PUBLICATIONS

Extended European Search Report for European Patent Application No. 22203560.2, mailed Mar. 22, 2023 (10 pages).

Xiao, F. et al., "An efficient phosphonate-based ionic liquid on flame retardancy and mechanical property of epoxy resin," J Mater Sci, 52:13992-14003 (2017).

Office Action for Korean Patent Application No. 10-2021-0143193, mailed Apr. 2, 2026 (14 pages).

*Primary Examiner* — Carlos Barcena

(74) *Attorney, Agent, or Firm* — Perkins Coie LLP

(57) ABSTRACT

Provided is an ionic liquid including a cationic compound represented by Formula (1), where R represents an N-containing heterocyclic cation, and an anionic compound, an electrolyte including the ionic liquid, and a secondary battery.

식 (1)

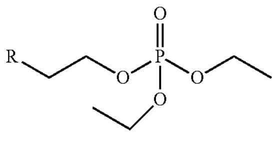

16 Claims, 1 Drawing Sheet

(a) (b) (c) (d)
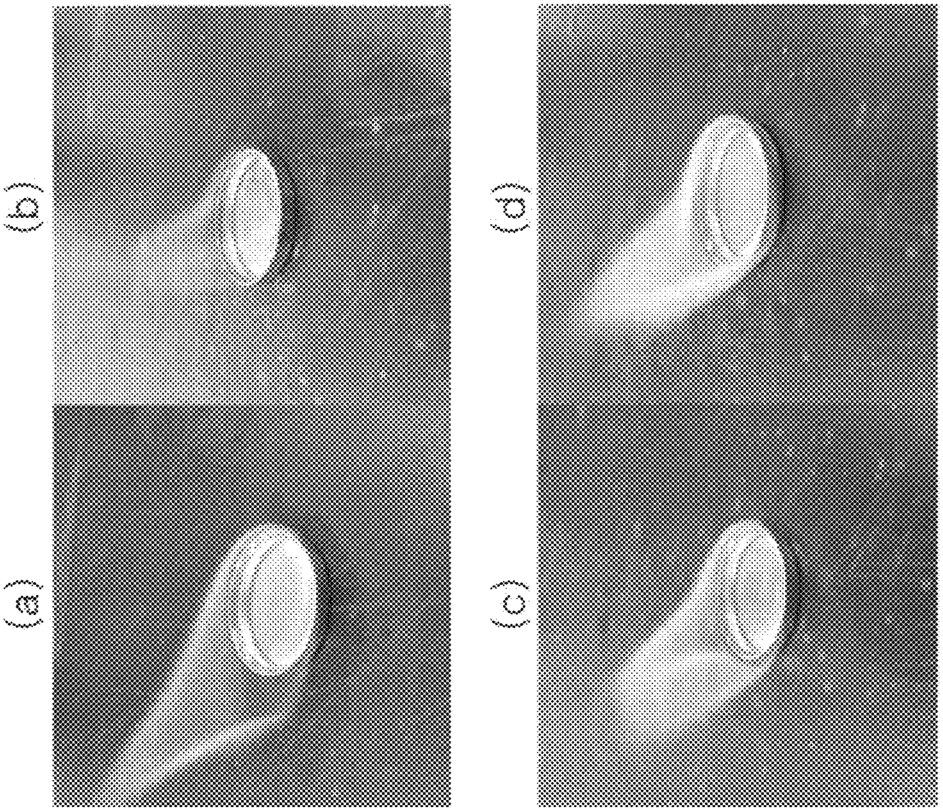

IONIC LIQUID, ELECTROLYTE FOR SECONDARY BATTERY INCLUDING IONIC LIQUID, AND SECONDARY BATTERY INCLUDING ELECTROLYTE

CROSS-REFERENCE TO RELATED APPLICATION(S)

This application claims the benefit of priority to Korean Patent Application No. 10-2021-0143193 filed on Oct. 26, 2021 in the Korean Intellectual Property Office, the disclosure of which is incorporated herein by reference in its entirety.

TECHNICAL FIELD

The present disclosure relates to an ionic liquid, an electrolyte for a secondary battery including the ionic liquid, and a secondary battery including the electrolyte.

BACKGROUND

With the technological development of mobile devices and electric vehicles and increasing demand for mobile devices and the electric vehicles, demand for secondary batteries as an energy source has been rapidly increasing. Accordingly, a large amount of research has been conducted into secondary batteries capable of satisfying various needs. In particular, there is high demand for lithium secondary batteries such as lithium ion batteries and lithium ion polymer batteries having excellent energy density, discharge voltage, and output stability.

SUMMARY

In various implementations, a lithium secondary battery may be manufactured by impregnating a prepared electrode assembly of a positive electrode/separator/negative electrode with an electrolyte containing lithium salt using a lithium transition metal oxide or a composite oxide as a positive electrode active material and a carbon-based material or silicon-based material as a negative electrode active material.

There may be an issue in which a lithium secondary battery using a lithium transition metal oxide or a composite oxide is disposed in a thermally unstable state when stored at high temperature in a fully charged state because a metal component is released from a positive electrode of the battery. For example, the oxygen released from the positive electrode may accelerate an exothermic decomposition reaction of an electrolyte solvent, causing a so-called swelling phenomenon in which the battery swells. Due to such a swelling phenomenon, a lifespan and charging/discharging efficiency of the battery are rapidly reduced. In some cases, the safety of the battery is greatly reduced, such as in an explosion of the battery.

In order to improve the flame retardant properties of the electrolyte, a flame retardant compound such as an ionic liquid may be added to the electrolyte. However, when 20 wt % or more of an ionic liquid is added based on the electrolyte composition so as to secure flame retardant properties, an initial irreversible capacity may be significantly high due to a side reaction of graphite, which is a negative electrode active material, making it impossible to drive a secondary battery cell.

An aspect of the present disclosure provides an ionic liquid capable of reducing irreversible capacity of a secondary battery while securing flame retardancy of an electrolyte, an electrolyte for a secondary battery including the ionic liquid, and a secondary battery including the electrolyte.

According to an aspect of the present disclosure, provided is an ionic liquid including a cationic compound represented by Formula (1) below, and an anionic compound.

(1)

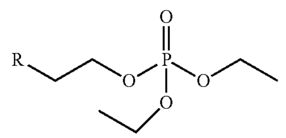

(In Formula (1), R represents an N-containing heterocyclic cation.)

The R may be pyridinium, pyridazinium, pyrrolidnium, pyrimidinium, pyrazinium, imidazolium, pyrazolium, thiazolium, oxazolium, or triazolium.

The cationic compound may be at least one selected from the group represented by one or more of Formulas (2) to (4) below:

(2)

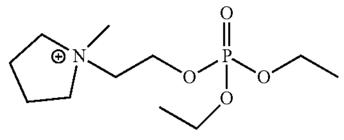

(3)

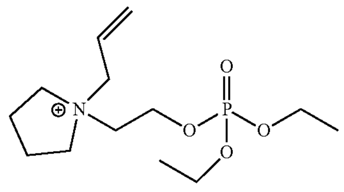

(4)

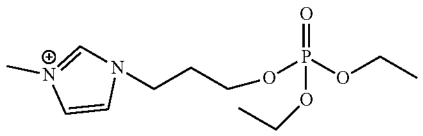

The anionic compound may be one of trifluoromethyl sulfonylimide (TFSI), bis(fluorosulfonyl)imide (FSI), chloride (Cl), dicyanamide (DCA), trifluoromethanesulfonate (Otf), acetate (Ac), hydrate (OH), diethylphosphate (DEP), thiocyanate (SCN), or methylsulfate (MeSO4).

The ionic liquid may include a cationic compound and an anionic compound selected from a group represented by Formulas (5) to (7) below:

(5)

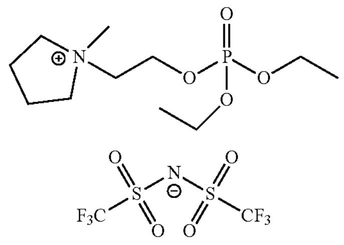

-continued (6)

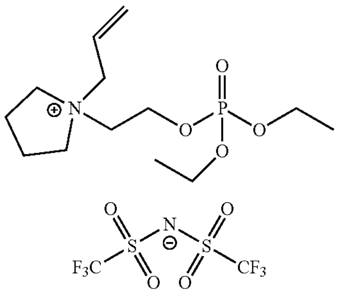

(7)

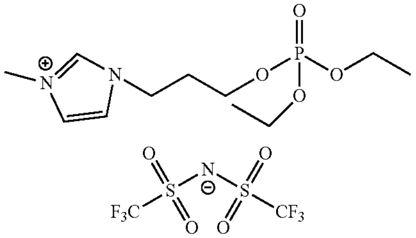

According to another aspect of the present disclosure, provided is an electrolyte for a secondary battery including the ionic liquid, a lithium salt, and a solvent.

An amount of the ionic liquid may be 3 to 10 wt % based on the total weight of the electrolyte.

The cationic compound may include a compound represented by one of Formulas (2) to (4) below:

(2)

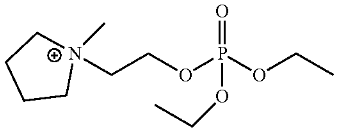

(3)

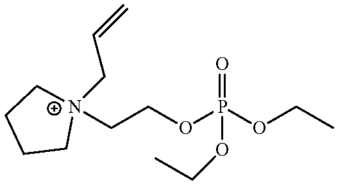

(4)

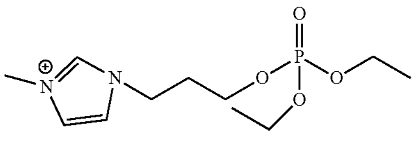

In some implementations, the anionic compound may include trifluoromethyl sulfonylimide (TFSI), bis(fluorosulfonyl)imide (FSI), chloride (Cl), dicyanamide (DCA), trifluoromethanesulfonate (Otf), acetate (Ac), hydrate (OH), diethylphosphate (DEP), thiocyanate (SCN), or/and methyl sulfate (MeSO4).

The ionic liquid may include a cationic compound and an anionic compound selected from the group represented by Formulas (5) to (7) below:

(5)

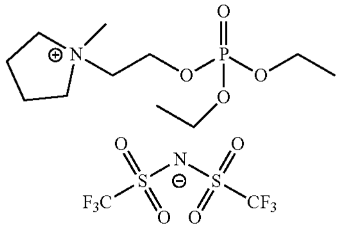

(6)

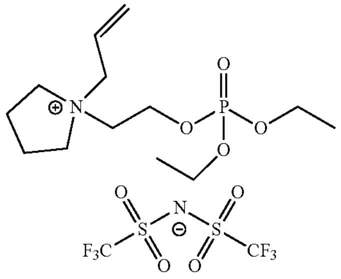

(7)

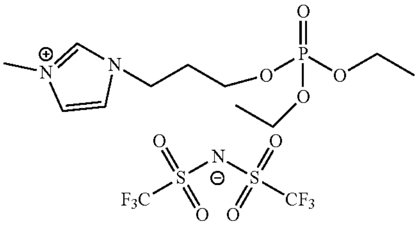

The electrolyte may further include a negative electrode protective film former.

The negative electrode protective film former may include lithium bisoxalato borate (LiBOB) lithium difluoro(oxalato) borate (LiFOB), maleic anhydride, and/or lithium difluoro-bis-(oxalate) phosphate (W2).

An amount of the negative electrode protective film former may be 0.2 to 2 wt % based on the total weight of the electrolyte.

According to another aspect of the present disclosure, provided is a secondary battery including the electrolyte, a positive electrode, a negative electrode, and a separator interposed between the positive electrode and the negative electrode.

The electrolyte may include 3 to 10 wt % of an ionic liquid based on the total weight of the electrolyte.

The cationic compound may include a compound represented by one of the Formulas (2) to (4) below:

(2)

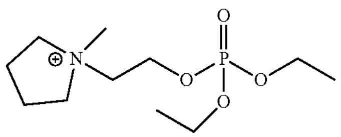

(3)

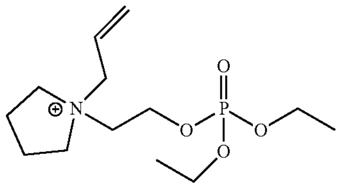

-continued (4)

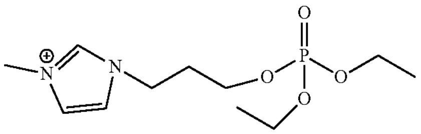

In some implementations, the anionic compound may be trifluoromethyl sulfonylimide (TFSI), bis(fluorosulfonyl) imide (FSI), chloride (Cl), dicyanamide (DCA), trifluoromethanesulfonate (Otf), acetate (Ac), hydrate (OH), diethylphosphate (DEP), thiocyanate (SCN), and/or methyl sulfate (MeSO4).

The ionic liquid may include a cationic compound and an anionic compound selected from the group represented by Formulas (5) to (7) below:

(5)

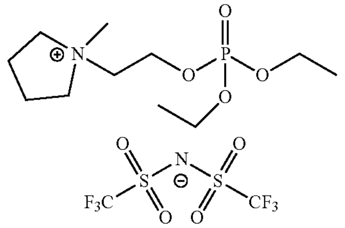

(6)

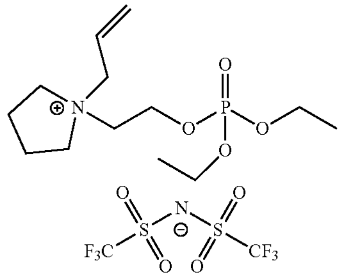

(7)

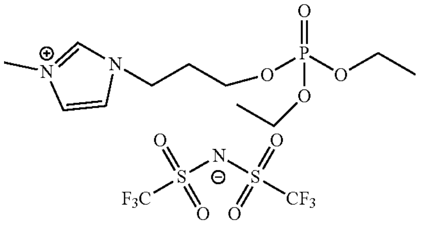

The electrolyte may further include a negative electrode protective film former.

The negative electrode protective film former may include at least one selected from lithium bisoxalato borate (LiBOB) lithium difluoro(oxalato)borate (LiFOB), maleic anhydride, and/or lithium difluorobis-(oxalate) phosphate (W2).

An electrolyte for a secondary battery including an ionic liquid according to the present disclosure may improve safety of the secondary battery by improving flame retardancy. In addition, even when a negative electrode film former is included, an irreversible capacity of the secondary battery may be reduced.

BRIEF DESCREPTION OF DRAWINGS

The above and other aspects, features, and advantages of the present disclosure will be more clearly understood from the following detailed description, taken in conjunction with the accompanying drawings, in which:

The FIGURE shows images of flames taken in order when three seconds have elapsed after ignition in electrolytes of Comparative Example 1 and Examples 1 to 3.

DETAILED DESCRIPTION

Hereinafter, preferred example embodiments of the present disclosure will be described with reference to various examples. However, the example embodiments of the present disclosure may be modified in various different forms, and the scope of the present disclosure is not limited to the example embodiments described below.

The present disclosure relates to an ionic liquid and an electrolyte for a secondary battery including the ionic liquid. In order to improve flame retardant properties of the electrolyte, a technology using the ionic liquid has been studied, but the use of the ionic liquid for improving the flame retardant properties has an issue in that an initial irreversible capacity may be very high due to a side reaction with graphite, which is a negative electrode active material. The inventors have found that when an ionic liquid including a specific cationic compound and anionic compound is provided, the flame retardant properties may be improved as well as the initial irreversible capacity may be reduced. Based on these findings, the inventors have completed the present disclosure.

According to one aspect of the present disclosure, provided is an ionic liquid including a cationic compound represented by Formula (1), and an anionic compound.

(1)

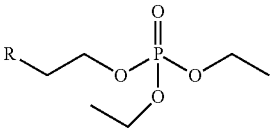

In Formula (1), R represents an N-containing heterocyclic cation.

The ionic liquid represents a salt in a liquid state including only ions, and the cationic compound of the ionic liquid according to the present disclosure may include a structure in which one or more cations are attached to a phosphate functional group. As such, the cationic compound may include the phosphate functional group, thereby improving flame retardant performance of an electrolyte.

In the cationic compound, R represents an N-containing heterocyclic cation, for example, may be pyridinium, pyridazinium, pyrimidinium, pyrazinium, pyrrolidinium, imidazolium, pyrazolium, thiazolium, oxazolium, or triazolium. More specifically, R may be pyrrolidinium or imidazolium.

The cationic compound may be, for example, compounds represented by Formulas (2) to (4), and one or two or more of the compounds may be selected.

(2)

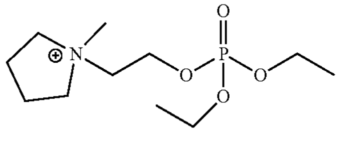

-continued (3)

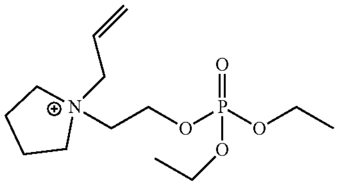

(4)

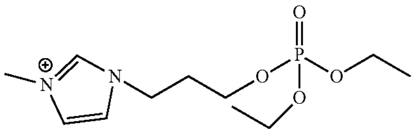

The anionic compound is not particularly limited, but may include at least one of trifluoromethylsulfonylimide (TFSI), bis(fluorosulfonyl)imide (FSI), chloride (Cl), dicyanamide (DCA), trifluoromethanesulfonate (Otf), acetate (Ac), hydrate (OH), diethylphosphate (DEP), thiocyanate (SCN) or methyl sulfate (MeSO4) in some implementations. As a specific example, the anionic compound may include bis (fluorosulfonyl)imide which may be represented by the following structural formula.

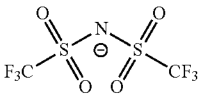

As described above, the present disclosure provides an ionic liquid including a specific cationic compound and anionic compound, but the ionic liquid according to the present disclosure is not limited thereto, for example, may be selected from the group represented by Formulas (5) to (7).

(5)

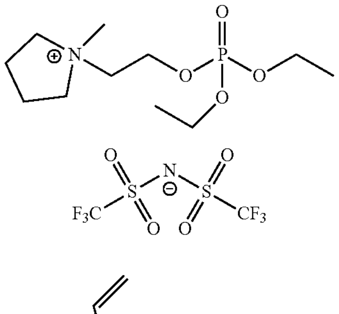

(6)

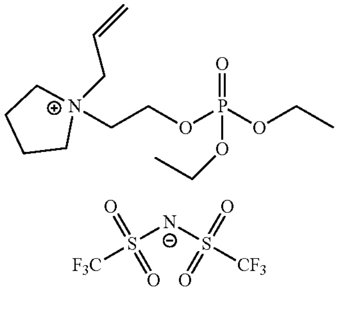

-continued (7)

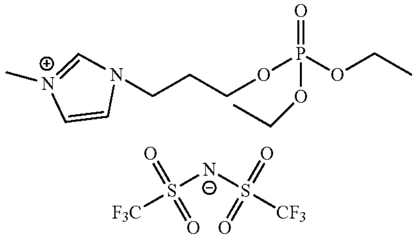

The ionic liquid including the structure according to the present disclosure may have a reduction potential lower than those of other substances, thereby reducing side reactions with a negative electrode. Thus, the ionic liquid may be suitably added to the electrolyte of the secondary battery.

According to another aspect of the present disclosure, provided is an electrolyte for a secondary battery including the above-described ionic liquid, a lithium salt, and a solvent.

An amount of the ionic liquid may be 3 to 10 wt % based on the total weight of the electrolyte. When the amount of the ionic liquid is less than 3 wt %, the flame retardant properties may be very insignificant, so there may be no effect of improving the flame retardancy of the electrolyte. When the amount of the ionic liquid is greater than 10 wt %, the flame retardant properties may be secured. However, an excessive reaction with an electrode may occur due to a high amount of the ionic liquid, and a secondary battery cell may have very poor performance due to a decrease in capacity retention rate and an increase in resistance.

According to another example embodiment of the present disclosure, the electrolyte may further include a negative electrode protective film former. The negative electrode protective film former added to the electrolyte may be decomposed during an initial charge/discharge process to form a protective film on a negative electrode, thereby suppressing the decomposition of the electrolyte.

Specifically, the ionic liquid may have slightly low reduction stability, so decomposition may occur in the negative electrode, and over-decomposition may occur when the amount of the ionic liquid is 10 wt % or more. Accordingly, cell performance may be very poor. When a negative electrode film additive is added to suppress the decomposition of the ionic liquid, the decomposition of the ionic liquid may be partially suppressed, thereby further improving the cell performance.

The negative electrode protective film former is not particularly limited, but may include at least one of lithium bisoxalato borate (LiBOB), lithium difluoro(oxalato)borate (LiFOB), maleic anhydride, or/and lithium difluorobis-(oxalato) phosphate (W2). For example, the negative electrode protective film former may include LiBOB or LiFOB in some implementations.

An amount of the negative electrode protective film former may be 0.2 to 2 wt % based on the total weight of the electrolyte. When the amount of the negative electrode protective film former is less than 0.2 wt %, the negative electrode film may not be sufficiently formed, so that the decomposition of the ionic liquid may not be sufficiently suppressed. When the amount of the negative electrode protective film former is more than 2 wt %, gas may be generated due to over-decomposition of the negative electrode film former, which may cause a reduction in performance of the secondary battery.

The electrolyte according to the present disclosure may include a lithium salt and a solvent, and the lithium salt and the solvent are not particularly limited.

For example, the lithium salt may include at least one of $LiPF_6$, $LiClO_4$, $LiAsF_6$, $LiBF_4$, $LiSbF_6$, $LiAlO_4$, $LiAlCl_4$, $LiCF_3SO_3$, $LiC_4F_9SO_3$, $LiN(C_2F_5SO_3)_2$, $LiN(C_2F_5SO_2)_2$, $LiN(CF_3SO_2)_2$. $LiN(CxF_{2x+1}SO_2)(CyF_{2y+1}SO_2)$ (where x and y are integers greater than or equal to 0), LiCl, LiI, LiSCN, $LiB(C_2O_4)_2$, $LiF2BC_2O_4$, $LiPF_4(C_2O_4)$, $LiPF_2(C_2O_4)_2$, or/and $LiP(C_2O_4)_3$.

In addition, the solvent may include at least one of ester-based, sulfone-based, ether-based or/and nitrile-based organic solvents. Specifically, a base solvent may include at least one of propylene carbonate, ethylene carbonate, 2,3-butylene carbonate, diethyl carbonate, dimethyl carbonate, dipropyl carbonate, ethyl methyl carbonate, methyl propyl carbonate, dibutyl carbonate, methyl butyl carbonate, methyl isopropyl carbonate, methyl ester, methyl formate, methyl acetate, N,N-dimethylacetamide, fluoroethylene carbonate, methyl propionate, ethyl propionate, ethyl acetate, γ-butyrolactone, tetrahydrofuran, 2-methyltetrahydrofuran, 1,3-dioxolane, 4-methyl-1,3-dioxolane, dimethoxymethane, 1,2-dimethoxyethane, 1,2-dimethoxypropane, triethylene glycol dimethyl ether, dimethyl sulfone, dimethyl ether, ethylene sulfite, propylene sulfite, dimethyl sulfite, diethyl sulfite, or/and crown ether.

According to another aspect of the present disclosure, provided is a secondary battery including a negative electrode, a positive electrode, a separator interposed between the negative electrode and the positive electrode, and the electrolyte. As described above, the electrolyte including the ionic liquid according to the present disclosure may improve safety of the secondary battery by improving flame retardancy, and may reduce an irreversible capacity of the secondary battery when a negative electrode film former is further included.

The positive electrode, the negative electrode, and the separator included in the secondary battery are not particularly limited, and all positive electrodes, negative electrodes and separators recognized in the art may be applied without limitation.

For example, in the case of the positive electrode, a positive electrode current collector is not particularly limited, but a thin plate formed of an aluminum, stainless steel, or nickel material may be used, and a thin plate formed of an aluminum material may be preferably used. In addition, a porous body having a net shape or mesh shape may be used, and may be coated with an oxidation-resistant metal or alloy film to prevent oxidation.

The positive electrode active material, a compound capable of reversible intercalation and deintercalation of lithium, may specifically include a lithium transition metal composite oxide including lithium and at least one transition metal selected from at least one of nickel, cobalt, manganese or aluminum, and may preferably include, in some implementations, a lithium transition metal composite oxide including lithium and a transition metal including nickel, cobalt and manganese.

The positive electrode may further include one or more conductive materials selected from graphite, carbon black, a carbon nanotube, metal powder, or/and a conductive oxide so as to improve the conductivity.

The positive electrode may further include a binder to improve binding of the positive electrode active material and the conductive material and adhesive strength for the current collector. Specifically, the binder may include at least one selected from polyvinylidene fluoride, polyvinyl alcohol, carboxymethyl cellulose (CMC), starch, hydroxypropylcellulose, regenerated cellulose, polyvinylpyrrolidone, tetrafluoroethylene, polyethylene, polypropylene, ethylene-propylene-diene terpolymer (EPDM), sulfonated EPDM, styrene-butadiene rubber, or/and fluororubber. In some implementations, the binder may preferably include polyvinylidene fluoride.

In the case of the negative electrode, a negative electrode current collector is not particularly limited as long as it has conductivity without causing a chemical change in a corresponding battery. For example, copper, stainless steel, aluminum, nickel, titanium, sintered carbon, copper that is surface-treated with carbon, nickel, titanium, silver, and the like, stainless steel that is surface-treated with carbon, nickel, titanium, silver, and the like, an aluminum-cadmium alloy, and the like may be used. In addition, as in the case of the positive electrode current collector, bonding strength of the negative electrode active material may be increased by forming microscopic irregularities on a surface thereof. The negative electrode current collector may be used in various forms such as a film, a sheet, a foil, a net, a porous body, a foam body, a non-woven fabric body, and the like.

The negative electrode active material may be a silicon-based negative electrode active material and a carbon-based negative electrode active material.

Although not particularly limited, the silicon-based negative electrode active material may use or include at least one selected from an SiOx ($0 \le x < 2$) particle, a Si—C composite, and a Si—Y alloy (where Y is at least one selected from the group consisting of an alkali metal, an alkaline earth metal, a transition metal, a group 13 element, a group 14 element, or/and a combination thereof. In some implementations, for example, the silicon-based negative electrode active material may be or include SiO.

The carbon-based negative electrode active material may be, for example, at least one selected from artificial graphite, natural graphite, or/and a graphitized meso-carbon microbead. In some implementations, the carbon-based negative electrode active material may specifically be or include an artificial graphite.

The negative electrode may include a binder and a conductive material, together with the negative electrode active material.

The binder may include an aqueous binder and a rubber-based binder, and the aqueous binder that is soluble in an aqueous solvent such as water may include at least one selected from polyvinyl alcohol (PVA), polyacrylic acid (PAA), polyethylene glycol (PEG), polyacrylonitrile (PAN), polyacryl amide (PAM), and carboxyl methyl cellulose (CMC).

The rubber-based binder may not be properly dissolved in an aqueous solvent such as water, but may be defined as being able to be smoothly dispersed in the aqueous solvent. Specifically, the rubber-based binder may include at least one selected from styrene butadiene rubber (SBR), hydrogenated nitrile butadiene rubber (HNBR), acrylonitrile butadiene rubber, acrylic rubber, butyl rubber, or/and fluoro rubber. In some implementations, the rubber-based binder may specifically include at least one of styrene butadiene rubber or/and hydrogenated nitrite butadiene rubber in terms of easy dispersion and excellent phase stability. In some implementations, the rubber-based binder may be or include a styrene-butadiene rubber.

The conductive material may be at least one selected from graphite, carbon black, a carbon nanotube, metal powder, or/and a conductive oxide.

As the separator, a porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith, or a porous non-woven fabric, for example, a non-woven fabric formed of a high melting point glass fiber or a polyethylene terephthalate fiber may be used, but the present disclosure is not limited thereto.

A secondary battery module may be configured using the secondary battery as a unit cell, and one or more of the modules may be packaged in a pack case to form a secondary battery pack. The above-described secondary battery module and a secondary battery pack including the secondary battery module may be applied to various devices. Such devices may be applied lb to transportation devices such as an electric bicycle, an electric vehicle, and a hybrid vehicle, but the present disclosure is not limited thereto, and is applicable to various devices capable of using the secondary battery module and the secondary battery pack including the secondary battery module, which is also within the scope of the present disclosure.

Hereinafter, the present disclosure will be described in more detail through specific examples. The following examples are only examples to assist in understanding of the present disclosure, and the scope of the present disclosure is not limited thereto.

EXAMPLES

Comparative Example 1

An electrolyte was prepared by inputting LiPF6 of 1M, and 1 mass % of fluoro-ethylene carbonate (FEC), 0.5 mass % of propene sultone (PRS), 1 mass % of $LiPO_2F_2$, 0.5 mass % of propane sultone (PS), 0.5 mass % of ethylene sulfate (ESA), and a remainder solvent (EC:EMC in a volume ratio of 25:75) as an additive.

Example 1

An electrolyte composition was prepared by mixing an ionic liquid including a cationic compound and an anionic compound represented by Formula (7) with the electrolyte prepared in Comparative Example 1 at a ratio of 10 wt % based on the total weight of the electrolyte.

Example 2

An electrolyte composition was prepared in the same manner as in Example 1, except that the ionic liquid represented by Formula (5) was mixed instead of the ionic liquid represented by Formula (7).

Example 3

An electrolyte composition was prepared in the same manner as in Example 1, except that the ionic liquid represented by Formula (6) was mixed instead of the ionic liquid represented by Formula (7).

After igniting electrolyte compositions having the same weight according to Comparative Example 1 and Examples 1 to 3, time required until being extinguished was measured, and results thereof are indicated in Table 1 as self-extinguishing time.

In addition, a temperature of a cell was raised to 150° C. with respect to the same cell, except that the electrolytes of Comparative Example 1 and Examples 1 to 3 were used, and time required until the cell explodes (a high-temperature box test and a hot box test) and a calorific value were measured, and time additionally required to explode as compared to time required for the cell of Comparative Example 1 to explode is indicated in Table 1 as delay time.

TABLE 1

| Analysis of flame retardant properties | Comparative Example 1 | Example 1 | Example 2 | Example 3 |
|---|---|---|---|---|
| Self-extinguishing time (sec) | 60 | 45 | 48 | 51 |
| Hot box test Delay time (sec) | — | +4.2 | +0.7 | +1.5 |
| Calorific value (J/g) | 288 | 221 | 251 | 233 |

The figure is an image of a frame taken when three seconds have elapsed after ignition in the electrolyte compositions of Comparative Example 1 (Panel (a)), Example 1 (Panel (b)), Example 2 (Panel (c)), and Example 3 (Panel (d)). Referring to Table 1 and the figure, it can be confirmed that Examples 1 to 3 had a significantly shorter self-extinguishing time and a lower calorific value as compared to those of Comparative Example 1.

In addition, in the high-temperature box test, it can be confirmed that time required until an explosion occurs was delayed as compared to that of Comparative Example 1. In particular, the electrolyte composition according to Example 1 exhibited a most excellent effect.

After preparing a secondary battery cell using, as an electrolyte, the electrolyte compositions according to Comparative Example 1 and Examples 1 to 3, an initial capacity and a DCIR were measured, and results thereof are indicated in Table 2. Thereafter, the secondary battery cell was maintained at 60° C. for five weeks and a high-temperature storage experiment was conducted thereon, and then a DCIR, a capacity retention rate, and a thickness increase rate were measured, and results thereof are indicated in Table 3.

TABLE 2

| | Comparative Example 1 | Example 1 | Example 2 | Example 3 |
|---|---|---|---|---|
| Capacity [mAh] | 1750 | 1633 | 1437 | 1590 |
| DCIR [mΩ] | 100% | 93% | 82% | 90% |

TABLE 3

| | Comparative Example 1 | Example 1 | Example 2 | Example 3 |
|---|---|---|---|---|
| DCIR [mΩ] | 31.1 | 41.0 | 76.1 | 44.8 |
| Capacity retention rate [%] | 93 | 85 | 70 | 82 |
| Thickness increase rate [%] | 14 | 20 | 27 | 40 |

Referring to Tables 2 and 3, in Examples 1 to 3, the cell had slightly reduced performance due to input of the ionic liquid, but the performance was sufficient for commercialization. In particular, as indicated in Table 1, in Example 1, it can be confirmed that a decrease in performance was insignificant while the flame retardant properties were significantly improved.

While example embodiments have been shown and described above, variations and enhancements of the disclosed example embodiments and other embodiments may be made based on what is disclosed in this patent document.

What is claimed is:

1. An ionic liquid comprising:

a cationic compound represented by Formulas (1), (3), or (4) below:

(1)

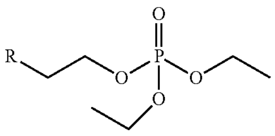

(3)

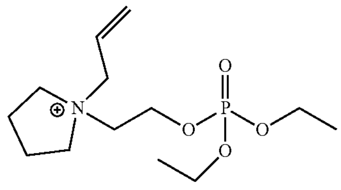

(4)

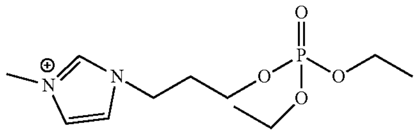

wherein R is pyridinium, pyridazinium, pyrimidinium, pyrazinium, imidazolium, pyrazolium, thiazolium, oxazolium, or triazolium; and an anionic compound.

2. The ionic liquid of claim 1, wherein the anionic compound includes trifluoromethyl sulfonylimide (TFSI), bis (fluorosulfonyl) imide (FSI), chloride (Cl), dicyanamide (DCA), trifluoromethanesulfonate (Otf), acetate (Ac), hydrate (OH), diethylphosphate (DEP), thiocyanate (SCN), or methylsulfate (MeSO4).

3. The ionic liquid of claim 1, wherein the ionic liquid comprises a cationic compound and an anionic compound selected from the group represented by Formulas (6) and (7) below:

(6)

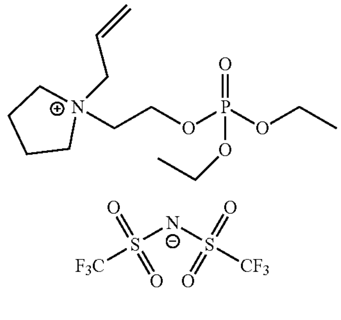

-continued (7)

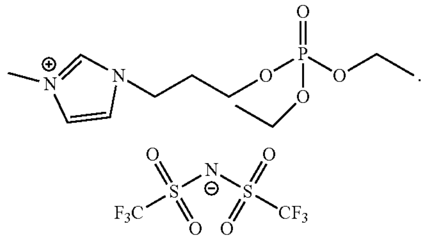

4. An electrolyte for a secondary battery comprising:

an ionic liquid comprising:

a cationic compound represented by Formulas (1), (3), or (4) below:

(1)

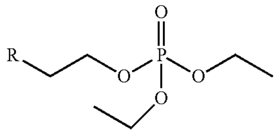

(3)

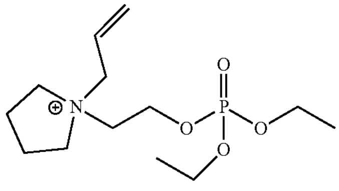

(4)

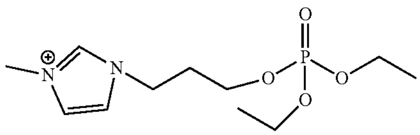

wherein R is pyridinium, pyridazinium, pyrimidinium, pyrazinium, imidazolium. pyrazolium, thiazolium, oxazolium, or triazolium;

an anionic compound;

a lithium salt; and a solvent.

5. The electrolyte of claim 4, wherein an amount of the ionic liquid is 3 to 10 wt % based on the total weight of the electrolyte.

6. The electrolyte of claim 4, wherein the anionic compound includes at least one selected from trifluoromethyl sulfonylimide (TFSI), bis (fluorosulfonyl) imide (FSI), chloride (Cl), dicyanamide (DCA), trifluoromethanesulfonate (Otf), acetate (Ac), hydrate (OH), diethylphosphate (DEP), thiocyanate (SCN), or methyl sulfate (MeSO4).

7. The electrolyte of claim 4, wherein the ionic liquid comprises a cationic compound and an anionic compound selected from the group represented by Formulas (6) and (7) below:

(6)

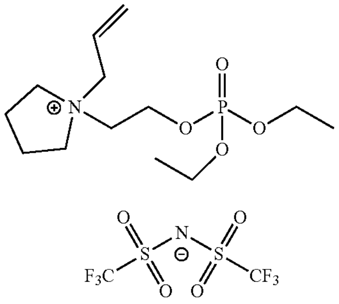

(7)

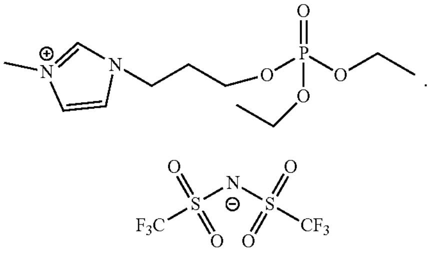

8. The electrolyte of claim 4, further comprising:

a negative electrode protective film former.

9. The electrolyte of claim 8, wherein the negative electrode protective film former comprises at least one selected from lithium bisoxalato borate (LiBOB) lithium difluoro (oxalato) borate (LiFOB), maleic anhydride, or lithium difluorobis-(oxalate) phosphate (W2).

10. The electrolyte of claim 8, wherein an amount of the negative electrode protective film former is 0.2 to 2 wt % based on the total weight of the electrolyte.

11. A secondary battery comprising:

the electrolyte of claim 4;

a positive electrode;

a negative electrode; and a separator interposed between the positive electrode and the negative electrode.

12. The secondary battery of claim 11, wherein the electrolyte comprises 3 to 10 wt % of an ionic liquid based on the total weight of the electrolyte.

13. The secondary battery of claim 11, wherein the anionic compound includes at least one of trifluoromethyl sulfonylimide (TFSI), bis (fluorosulfonyl) imide (FSI), chloride (Cl), dicyanamide (DCA), trifluoromethanesulfonate (Otf), acetate (Ac), hydrate (OH), diethylphosphate (DEP), thiocyanate (SCN), or methyl sulfate (MeSO4).

14. The secondary battery of claim 11, wherein the ionic liquid comprises a cationic compound and an anionic compound selected from a group represented by Formulas (6) and (7) below:

(6)

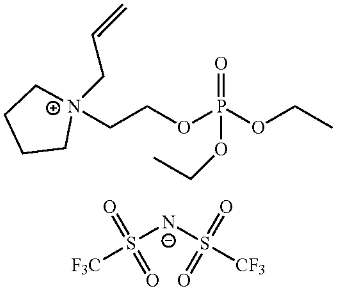

(7)

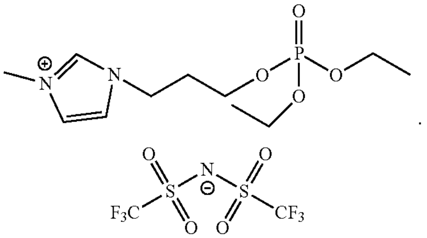

15. The secondary battery of claim 11, wherein the electrolyte further comprises a negative electrode protective film former.

16. The secondary battery of claim 15, wherein the negative electrode protective film former comprises at least one of lithium bisoxalato borate (LiBOB) lithium difluoro (oxalato) borate (LiFOB), maleic anhydride, or lithium difluoro bis-(oxalate) phosphate.

* * * * *